(12) United States Patent
Ahmad et al.

(10) Patent No.: US 10,682,385 B2
(45) Date of Patent: Jun. 16, 2020

(54) SAFFRON TREATMENT METHOD FOR MAMMALIAN MALADIES

(71) Applicants: Aftab Ahmad, Chicago, IL (US); Christine A. Frysz, Orchard Park, NY (US)

(72) Inventors: Aftab Ahmad, Chicago, IL (US); Christine A. Frysz, Orchard Park, NY (US)

(*) Notice: Subject to any disclaimer, the term of this patent is extended or adjusted under 35 U.S.C. 154(b) by 747 days.

(21) Appl. No.: 14/595,095

(22) Filed: Jan. 12, 2015

(65) Prior Publication Data

US 2015/0196613 A1 Jul. 16, 2015

Related U.S. Application Data

(60) Provisional application No. 61/926,241, filed on Jan. 10, 2014.

(51) Int. Cl.
| | |
|---|---|
| A61K 36/896 | (2006.01) |
| A61K 36/8967 | (2006.01) |
| A61K 36/88 | (2006.01) |
| A61M 11/00 | (2006.01) |
| A61M 15/00 | (2006.01) |
| A24F 47/00 | (2020.01) |
| A61M 11/06 | (2006.01) |
| A61K 9/00 | (2006.01) |
| A61M 15/06 | (2006.01) |

(52) U.S. Cl.
CPC ............ *A61K 36/88* (2013.01); *A24F 47/008* (2013.01); *A61M 11/005* (2013.01); *A61M 11/06* (2013.01); *A61M 15/009* (2013.01); *A61K 9/0073* (2013.01); *A61K 2236/00* (2013.01); *A61M 15/06* (2013.01)

(58) Field of Classification Search
CPC ...................................... A61K 36/185
USPC ........................ 424/774, 778, 779
See application file for complete search history.

(56) References Cited

U.S. PATENT DOCUMENTS

| | | | |
|---|---|---|---|
| 4,986,985 | A | 1/1991 | Grossman et al. |
| 5,178,865 | A | 1/1993 | Ho et al. |
| 6,607,756 | B1 | 8/2003 | Rosenstiel |
| 7,344,740 | B2 | 3/2008 | Vail, III et al. |

(Continued)

FOREIGN PATENT DOCUMENTS

CN 202407080 U * 9/2012

OTHER PUBLICATIONS

F.I. Abdullaev, J.J. Espinosa-Aguirre, "Biomedical properties of saffron and its potential use in cancer therapy and chemoprevention trials", Cancer Detection and Prevention 28 (2004) p. 426-432.

(Continued)

*Primary Examiner* — Michael Barker
*Assistant Examiner* — Deborah A Davis
(74) *Attorney, Agent, or Firm* — Lakeview Patents, LLC

(57) ABSTRACT

A variety of medicinal compounds comprising *Crocus sativus* for the treatment of a plurality of medical ailments are described. A method of creating a *Crocus sativus* extract is also described. In addition, a variety of embodiments and methods of utilizing inhalation therapeutic delivery mechanisms including nebulizers and vaporizers for the vaporization of *Crocus sativus* comprising medicinal compounds and extracts are disclosed.

19 Claims, 6 Drawing Sheets

(56) References Cited

U.S. PATENT DOCUMENTS

Figure 1:
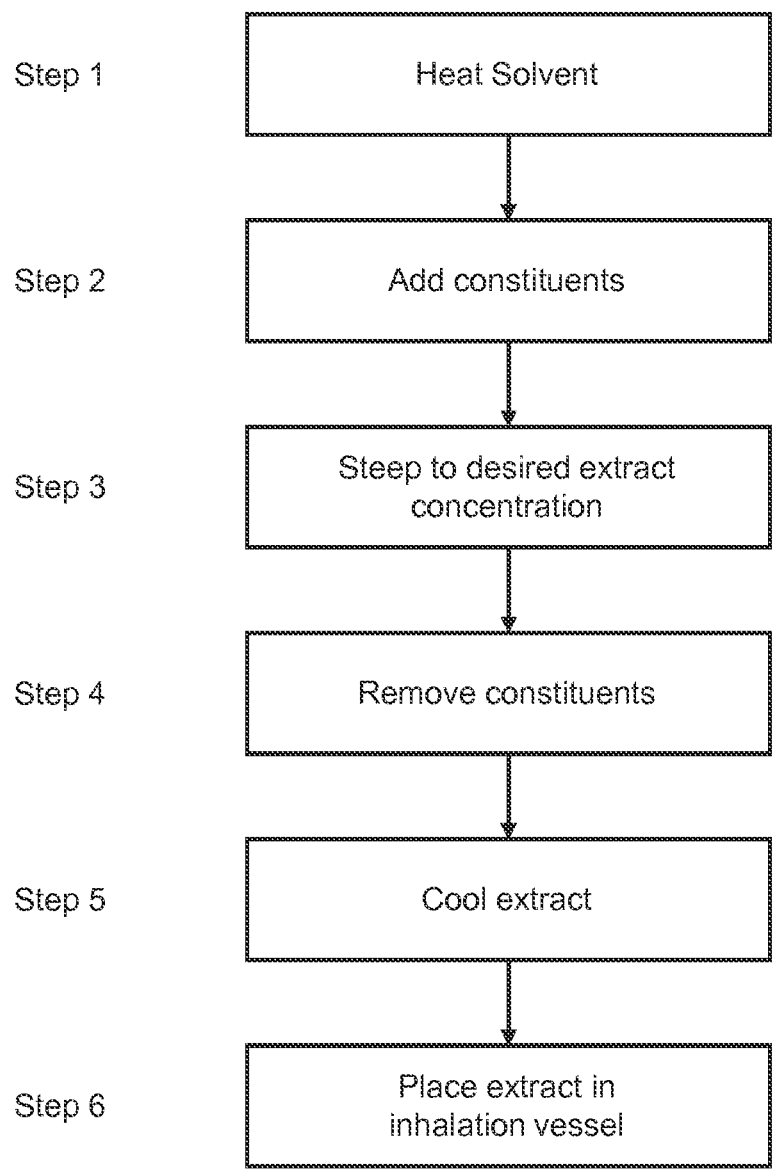

| | | | | |
|---|---|---|---|---|
| 8,235,213 B2* | 8/2012 | Berry | ............... | B65D 5/4802 206/461 |
| 8,550,069 B2* | 10/2013 | Alelov | ............... | A61M 11/005 128/202.21 |
| 8,569,247 B2 | 10/2013 | Eidenberger | | |
| 2003/0086981 A1 | 5/2003 | Seiki et al. | | |
| 2003/0140920 A1* | 7/2003 | Chaudry | ............... | A61K 9/0078 128/200.14 |
| 2005/0158411 A1* | 7/2005 | Vail, III | ............... | A61K 36/534 424/747 |
| 2007/0119450 A1* | 5/2007 | Wharton | ............... | A61M 15/00 128/200.23 |
| 2010/0210572 A1* | 8/2010 | Eidenberger | ............... | A61K 8/602 514/25 |
| 2012/0285236 A1* | 11/2012 | Haartsen | ............... | A61M 11/005 73/204.11 |
| 2013/0028993 A1* | 1/2013 | Kumar | ............... | A61K 36/23 424/725 |
| 2013/0037021 A1* | 2/2013 | Brewer | ............... | A61M 15/009 128/200.23 |

OTHER PUBLICATIONS

Akhondzadeh, S, et al., "Saffron in the treatment of patients with mild to moderate Alzheimer's disease: a 16-week, randomized and placebo-controlled trial", J Clin Pharm Ther Oct. 2010; 35(5) p. 581-588.

R. Srivastava, et al., "*Crocus sativus* L.: A comprehensive review", Pharmacogn Rev, Jul.-Dec. 2010; 4(8) p. 200-208.

M Agha-Hosseini, et al., "*Crocus sativus* L. (saffron) in the treatment of premenstrual syndrome: a double-blind, randomised and plecebo-controlled trial" BJOG 2008:115 p. 515-519.

Su Hee Jang, et al. "Effects and treatment methods of acupuncture and herbal medicine for premenstrual syndrome/premenstrual dysphoric disorder: systematic review" BMC Complementary and Alternative Medicine 2014, 14:11 p. 1-13.

Vijaya Bhargava K, "Medicinal Uses and Pharmacological Properties of *Crocus sativus linn* (Saffron)" International Journal of Pharmacy and Pharmaceutical Sciences, vol. 3, Suppl 3, 2011. p. 21-26.

Helmenstine, Anne Marie, "Steam Distillation Definition and Principle in Chemistry," ThoughtCo., Sep. 13, 2017.

* cited by examiner

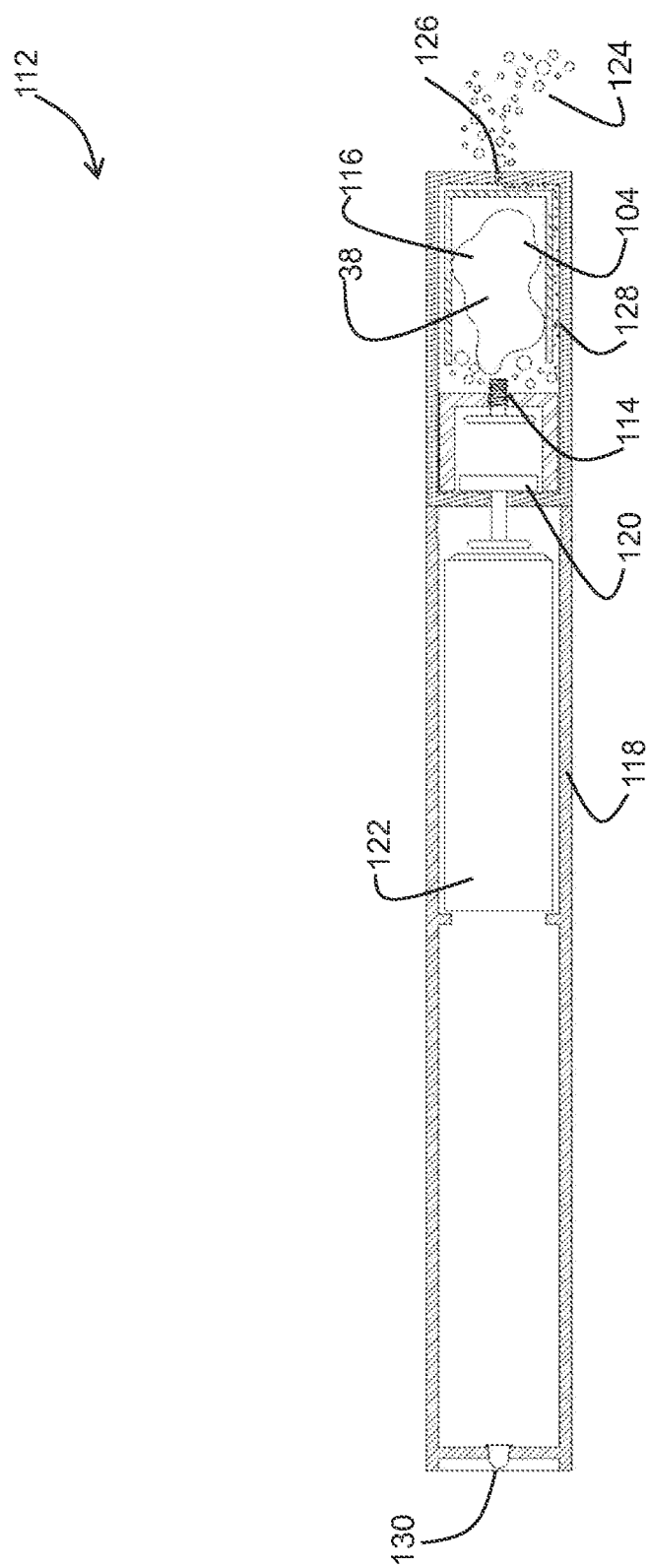

SAFFRON TREATMENT METHOD FOR MAMMALIAN MALADIES

CROSS-REFERENCE TO RELATED APPLICATION

The present application claims priority based on U.S. provisional application Ser. No. 61/926,241, filed Jan. 10, 2014.

BACKGROUND OF THE INVENTION

Field of the Invention

The present invention relates to herbal mixtures used in the treatment of medical maladies. More specifically, the present invention relates to herbal mixtures and extractions comprising *Crocus sativus* used to treat medical maladies.

Prior Art

A variety of herbal and plant extracts and preparations are available today for treating a variety of medical maladies affecting the mammalian body. Some preparations have been known for literally thousands of years while others are just being scientifically discovered to have curative effects. Effective plant extracts are highly desired as a "natural" way to treat medical maladies. It is believed that "natural" preparations will minimize potential adverse effects as compared to synthetic preparations. For example, U.S. Pat. No. 4,986,895 to Grossman et al., is directed to the use of water-soluble plant extracts for the treatment of virus skin infections. U.S. Pat. No. 5,178,865 to Ho et al., is directed to the use of Chinese herbal extracts for the treatment of HIV related disease. Ho discloses a total of 56 herbal extracts that were screened for anti-HIV activity using various in vitro techniques.

In particular, the medicinal properties of saffron (*Crocus sativus*) have been generally known as the herb has been used for many years in traditional medicine. Today, *Crocus sativus* is being scientifically investigated for its many medicinal benefits. The pistil of the crocus flower is composed of a stigma, a style, and an ovary. The stigma has a bright red color and contains many useful components including medicinal constituents, flavoring compounds and pigments. These useful components have been conventionally harvested from the pistils of open crocus flowers. Both the stigma and the petals of the crocus flowers are believed to possess medicinal properties. For example, both the saffron stigma and petals are said to be helpful for depression.

Saffron (*Crocus sativus*) has been the subject of numerous clinical investigations, examples of which are disclosed in articles by M. Agha-Hosseini et al., *BJOG* 2008, 115, p. 515-519; Su Hee Jang et al., *Complimentary and Alternative Medicine* 2014,14:11, p. 1-13; Vijaya Bhargava K, *International Journal of Pharmacy and Pharaceutical Sciences* 2011, vol. 3, suppl. 3, p. 22-26; F. I. Abdullaev et al., *Cancer Detection and Prevention* 2004, vol. 28, p. 426-432; and R. Srivastava et al., *Pharmacogn Rev.* 2010, Jul.-Dec., 4(8), p. 200-208, all of which are incorporated by reference herein. These investigations and others have identified the herb to comprise medicinal benefits for numerous medical ailments. Among these scientific studies, *Crocus sativus* has been identified as a sedative, a stimulant, in particular, a central nervous system stimulant, an antispasmodic, and a diaphoretic. Saffron, crocins and crocetin have been shown to inhibit breast cancer cell proliferation. It is used for the improvement of digestion and appetite and has been found to be extremely beneficial for providing relief from gas and acidity related problems. Saffron is also used for treating cough and is a known therapeutic for insomnia.

Saffron is also regularly used to treat many skin problems, for example, dry skin, and is used to lighten skin tone. *Crocus sativus* is used for the treatment of kidney, bladder and liver disorders. It is also believed that saffron helps to improve circulation of the organs of digestion. Saffron is considered by many to be a blood purifier and has been shown to have anti-inflammatory properties as well as help increase the oxygen content of blood, thus aiding in the overall health and well-being of a person. In addition, *Crocus sativus* has been used to treat asthma and atherosclerosis.

In addition, saffron has been used to help relieve inflammation associated with arthritis and also with providing relief from joint pain. It also has been shown to provide relief from lower back pain. Massaging the gums with saffron may help reduce soreness and inflammation of the mouth and the tongue.

Saffron has also been found to be effective in relieving symptoms of pre-menstrual symptoms (PMS). Saffron is even recommended for use during pregnancy as the herb is used to elevate body temperature. In addition, saffron is thought to be an antioxidant and have anti-cancerous and anti-tumor properties. It also may have a protective effect on the heart.

Prior art examples that demonstrate some of the medicinal uses of saffron can be found in U.S. Pat. No. 6,607,756 to Rosenstiel which discloses the use of pure powdered saffron to increase blood flow, to relieve pain and minimize skin dryness. U.S. Pat. App. Pub. No. 2003/0086981 to Seiki et al., discloses an ingestible saffron pill composed of a glycerin fatty acid ester that is used in the treatment of pre-menstrual symptoms (PMS). U.S. Pat. App. Pub. No. 2005/0158411 to Vail et al., now U.S. Pat. No. 7,344,740 discloses inhalation of a combination of peppermint oil complemented by saffron and other herbs that may be used to treat nausea induced by cancer chemotherapy treatment. U.S. Pat. No. 8,569,247 to Eidenberger, discloses embodiments of compositions derived from saffron and gardenia for medicinal treatments.

However, the prior art does not disclose saffron containing medicinal therapeutic mixtures that are designed to be vaporized or nebulized and, thus, provide treatment of these various medical ailments, such as pre-menstrual symptoms (PMS), through inhalation of a saffron comprising therapeutic aerosol. There exists, therefore, a need for a medicinal extract or therapeutic mixture comprising *Crocus sativus* to relieve medical ailments that is designed to be delivered through various inhalation methods. In addition, there exists a need for a medicinal extract or therapeutic mixture thereof comprising *Crocus sativus* that is designed to be vaporized or nebulized using various apparatus and inhalation methods.

Vaporization offers a means to extract and concentrate therapeutic agents, such as those separated from a naturally occurring plant, through a pure aerosol vapor mist. In an embodiment of the present invention, vaporization of plants, herbs, their extracts, and combinations thereof, is provided. In one such embodiment, the vaporization of *Crocus sativus* is provided. In the embodiment, the vaporization method utilizes different solvents and temperatures to modify and/or concentrate the therapeutic substance, for example, but not limited to, the saffron stigma, the saffron petals, dried saffron threads and powders. "Saffron threads" are generally known to be dried stigmas of the saffron plant.

An alternate delivery method is to inhale smoke resulting from the burning of a plant, herb or combination thereof. However, the burning process may create potentially toxic materials or compounds such as tars, which are generally not desirable. Hence, inhalation of vaporized saffron is preferred. Furthermore, the vaporizing process may be used to concentrate the therapeutic delivery agent. The separated agent from the naturally occurring plant may be also be otherwise concentrated using traditional processes such as, but not limited to, distillation. The concentrated end product may further be embodied in a delivery media or complemented by other therapeutic agents to enhance delivery and efficacy of therapy.

In the present application, embodiments and methods of preparing various medicinal compounds comprising *Crocus sativus*, infusions, extracts, and combinations thereof are provided. In addition, various means of vaporizing these medicinal extracts, infusions and compounds are provided. One such method of vaporizing and delivering a therapeutic compound to a patient is through the use of a nebulizer or inhaler.

Nebulizers and inhalers deliver a mist of the extraction or infusion of the therapeutic agent separated from a naturally occurring saffron plant, such as *Crocus sativus*. Nebulizers and inhalers are typically small devices that are used to administer various aerosol media through a traditional mouthpiece. Nebulizers generally operate by converting a therapeutic liquid medium into aerosol droplets that are inhaled by a user to provide therapy. Nebulizers typically use a gas, such as oxygen, or compressed air to "break up" a therapeutic solution or suspension into aerosol droplets that can be directly inhaled through a mouthpiece of the device. In addition, an ultrasonic transducer may also be provided that aids in the creation of the aerosol droplets. The term "aerosol" is defined herein as a mixture of gas and liquid particles. An example of an aerosol is mist, a mixture of vaporized water particles that are mixed with hot ambient air that cools down and condenses into a cloud of visible airborne water droplets.

There are generally two types of nebulizers, a jet nebulizer and an ultrasonic wave nebulizer. Both types of nebulizers are designed to administer a therapeutic medium to an individual via inhalation through a mouthpiece or a mask. It will be obvious to those skilled in the art that extended options for the final product achieved for vaporization also apply to nebulization.

A jet nebulizer or atomizer generally utilizes a compressor that causes a compressed gas, such as air or oxygen to flow at high velocity through a therapeutic liquid to convert the liquid into an aerosol. This aerosol is then inhaled by a patient. An ultrasonic wave nebulizer utilizes an electronic oscillator that generates a high frequency ultrasonic wave that causes the mechanical vibration of a piezoelectric element within the transducer. The transducer with it vibrating element is generally positioned within the therapeutic medium. The high frequency of the vibrating oscillator is generally sufficient to produce a vapor mist that is then inhaled.

In addition to a nebulizer, an inhaler may also be used to deliver the therapeutic medium to a patient. An inhaler typically comprises a sealed container having a release valve that is generally filled with a therapeutic medium such as a solvent or liquid extract. The therapeutic medium is typically housed under pressure within the container such that when the release valve is actuated, pressure from within the container causes the therapeutic medium to exit the container at a high velocity. A propellant may also be contained therewithin to aid in the expulsion of the therapeutic medium from the container. The propellant mixes with the therapeutic medium inside the container such that when the contents therewithin are released by the valve, an aerosol mixture of the therapeutic medium and propellant is expelled at a high velocity in an aerosol form. The container is received within an inhaler housing that comprises an activation mechanism capable of activating the release of the contents. The inhaler housing generally comprises a mouthpiece that directs the aerosol mixture into a patient. These and other embodiments will be disclosed in the specification and drawings of the present application.

BRIEF DESCRIPTION OF THE DRAWINGS

FIG. 1 is a flow chart of a preferred *Crocus sativus* extraction process of the present invention.

FIG. 2 illustrates a cross-sectional view of an embodiment of an inhaler device that may be used to deliver the *Crocus sativus* extract or therapeutic mixture thereof.

FIG. 3A shows a cross-sectional view of an embodiment of a jet nebulizer that may be used to deliver the *Crocus sativus* extract or therapeutic mixture thereof.

FIG. 3B is a cross-sectional view of an embodiment of an ultrasonic nebulizer that may be used to deliver the *Crocus sativus* extract or therapeutic mixture thereof.

FIG. 4 illustrates a cross-sectional view of an embodiment of a portable inhaler that may be used to deliver the *Crocus sativus* extract or therapeutic mixture thereof.

FIG. 5 is a cross-sectional view of an embodiment of an electronic cigarette which may be used to deliver the *Crocus sativus* extract or therapeutic mixture thereof.

SUMMARY OF THE PRESENT INVENTION

The present invention is directed to the use of saffron (*Crocus sativus*) in the treatment of various medical maladies affecting the mammalian body. *Crocus sativus*, commonly known as saffron, is a perennial stemless herb that is widely cultivated in different parts of the world, particularly Greece, India, Iran, and Spain. Saffron has been known to be used in traditional medicine as an anodyne, antidepressant, sedative, respiratory decongestant, anticatarrhal, expectorant, antispasmodic, eupeptic, stomachic, carminative, diaphoretic, gingival sedative, aphrodisiac, and emmenagogue.

In view of its wide range of medical uses, saffron has undergone extensive phytochemical and biochemical studies with a variety of biologically active constituents being isolated (Srivastava, R.). Chemical studies of *Crocus sativus* stigmas appear to indicate that it possesses medically beneficial carotenoids such as crocetin (also called α-crocetin or crocetin-I), its glycosidic forms being digentiobioside (crocin), gentiobioside, glucoside, gentioglucoside and diglucoside, γ-crocetin (monomethyl ester), γ-crocetin (dimethylester), trans crocetin isomer, 13-cis-crocetin, α-carotene, β-carotene, lycopene, zeaxanthin and mangicrocin, a xanthone-carotenoid glycosidic conjugate (Bhargava, V. K.). These carotenoids and other constituents contained within *Crocus sativus* are currently being investigated for a number of medical ailments, such as the treatment of Alzheimer's disease, respiratory disorders, Parkinson's disease seizures, diabetes, blood pressure disorders and cancer (Bhargava, V. K. and Abdullaev, F. I.). In addition, studies by M. Agha-Hosseini et al, have shown *Crocus sativus* to be particularly beneficial in the treatment of pre-menstrual symptoms.

The present invention, therefore, provides methods and embodiments for optimization of the medicinal benefits of saffron. Specifically, embodiments of *Crocus sativus* comprising extracts, compounds and mixtures are provided for use in the treatment of various medical ailments, particularly for the treatment of pre-menstrual symptoms.

In addition, embodiments and methods are provided for use of *Crocus sativus* comprising extracts, compounds and mixtures for use with various inhalation apparatus and methods such as vaporization and nebulization.

DESCRIPTION OF THE PREFERRED EMBODIMENTS

Before saffron can be used for its medicinal properties, it is first modified to extract, modify and concentrate the carotenoids comprised within the *Crocus sativus*. FIG. 1 is a flow chart that illustrates a preferred embodiment of the *Crocus sativus* extraction process of the present invention. In the embodiment, a constituent mixture comprising *Crocus sativus* is steeped in a heated solvent or liquid to extract and concentrate the *Crocus sativus* therewithin. The steeped *Crocus sativus* extract may then be mixed with other solvents and/or chemicals to further modify the medicinal mixture. This modification process preferably utilizes a steeping of the *Crocus sativus* combined with other optional herbs and extracts in a heated solvent. The steeping process preferably extracts and concentrates the carotenoids comprised within the *Crocus sativus*.

In a first step of the preferred process, a solvent, such as water is heated to a desired temperature. In step 2, the constituents comprising *Crocus sativus* are added to the heated solvent and are allowed to steep in the solvent for a period of time to thereby extract and concentrate the medicinal properties of the *Crocus sativus*. In the following step, the extract constituents are removed from the solvent and the extract is cooled, for example, to room temperature. The *Crocus sativus* concentrated extract is now ready to be utilized for therapeutic applications, particularly with an inhalation delivery device.

In addition, other constituents may also be added to the saffron and steeped together. Examples of additional non-limiting constituents that may be added to the mixture include herbs and spices such as turmeric, lavender, cinnamon, various mints, flavorings, vitamins, aromatics or other organic materials. In a preferred embodiment, at least one of the constituents may be soluble in water, ethyl alcohol or a mixture thereof.

In a preferred embodiment, *Crocus sativus* is added to water, such as distilled water. Other liquids or solvents such as, but not limited to, hydrocarbons, oils such as hemp and vegetable oils, alcohols such as ethyl alcohol, vegetable glycerins, tinctures, vinegar, glycerol, ether, infused liquids or combinations thereof, may be used as a steeping solvent. For the purpose of the present invention, the term "steep" is defined as soaking in a liquid such as water to soften, cleanse, extract or infuse a constituent. The term "extract" is defined herein as a preparation containing the active ingredient of a substance in concentrated form. The term "infusion" is defined herein as the extraction of an active substance through the use of steeping. The term "tincture" is defined herein as an extract from a plant or animal. Tinctures may comprise a variety of solvents including but not limited to ethyl alcohol, vinegar, glycerol, ether and propylene glycol. A tincture comprising *Crocus sativus* may be placed directly in the mouth, such as on the tongue or alternatively may be positioned within an inhaler, nebulizer, vaporizer or container thereof.

In a preferred embodiment, the solvent, such as water is first heated to about 100° C. (212° F.) at which point the solvent is removed from the heat source. Saffron is then added to the heated solvent, i.e., water, to extract and concentrate the *Crocus sativus*. The saffron may comprise any commercially available form. Non-limiting examples are as dried "threads", as a powder or combination thereof. In addition, the saffron may be contained within a fabric, a paper envelope or package such that the solvent and the *Crocus sativus* extract is able to permeate therethrough. The form of the package is non-limiting and may comprise a pouch, a pillow, a bag, or similar container. Alternatively, the saffron may be added directly into the solvent without being placed within a separate package or container. The steeped medium may be prepared in advance and may be bottled for future use.

The saffron may be steeped using a non-limiting combination of time intervals and solvent temperatures. For example, saffron may be steeped for a longer period of time in a solvent (i.e., water) having a temperature of 10° C. (50° F.) as compared to steeping in a solvent having a temperature of about 96° C. (205° F.). Table 1 shown below, illustrates an embodiment of the relationship between solvent temperature and steeping time. In a preferred embodiment, steeping time may range from about 30 seconds to about 15 minutes. However, a preferred steeping time ranges from about 1 minute to about 5 minutes.

TABLE 1

| Solvent Temperature (° C.) | Steeping Time (minutes) |
| --- | --- |
| 10 | 15 |
| 35 | 10 |
| 60 | 5 |
| 85 | 3 |
| 100 | 1 |

In addition, the amount of saffron added to the solvent also affects the optimal steeping time interval. In general, the more saffron added to the solvent, a longer steeping time is required to extract an effective therapeutic amount of *Crocus sativus*. A preferred steeping temperature is about 65° C. (150° F.) for a period of time commensurate with the amount of saffron added. Table 2 shown below, illustrates preferred steeping times for different amounts of saffron. These time intervals should be added to the previously given time intervals based on liquid temperature. For example, when steeping about one gram of saffron at 60° C., the total preferred steeping time is about 7 minutes, 5 minutes for 60° C. solvent (Table 1) and an additional 2 minutes for the additional 0.75 g of saffron.

TABLE 2

| Amount of Saffron (g) | Additional Steeping Time Interval (minutes) |
| --- | --- |
| 0.25 | 0 |
| 0.50 | 1 |
| 1.0 | 2 |
| 2.0 | 4 |
| 3.0 | 6 |

Color of the steeped solvent may be used as an indicator to determine the concentration level of extraction. The concentration level of extraction is important, as the darker the infused solvent appears, typically the more concentrated the *Crocus sativus* extract. Thus, concentration of the extract can be controlled by analysis of the color and hue of the appearance of the extract. Color intensity may range from a light yellow to a darker orange color. The longer the time interval the saffron is steeped at a given temperature, generally the deeper and darker the extract color and, subsequently, the more concentrated the infusion or extract. Also affecting color and infusion or extract concentration is the amount of saffron being steeped. In general, the greater the amount of saffron being steeped, the deeper and darker the color and, subsequently, the more concentrated the infusion or extract. Therapeutic saffron steep levels will vary from individual to individual. In a preferred embodiment, the concentration of *Crocus sativus* in the solvent is at least about 0.01 mg/ml. In a more preferred embodiment, the concentration of the *Crocus sativus* in the ranges from about 0.01 mg/ml to about 10 mg/ml. The solvent may comprise water, ethyl alcohol, or combinations thereof.

Once the saffron is steeped, the infused solvent may either be placed in a steamer or humidifier, a nebulizer, an aerosol delivery device, such as an inhaler or similar vaporizing or humidifying apparatus. Other therapeutic agents may be added to the infused solvent. Delivery of the vapor or mist may be assisted using oxygen, compressed air, or ultrasonic power.

A non-limiting example for preparing a steeped inhalation medium is as follows. Heat about 235 ml or about 235 g of water, preferably distilled water, to a temperature of about 100° C. Remove the water from the heat and allow the water to cool to a temperature of about 65° C. (150° F.) It is important to allow any solvent being used to steep saffron to cool to at least 65° C. (150° F.) before steeping, otherwise the therapeutic advantage of the steeped agent may be significantly diminished, and might even be rendered ineffective.

After the solvent reaches the desired temperature, about 0.25 g of the *Crocus sativus* stigma or other saffron form is added to the heated solvent and allowed to steep from about 5 to about 10 minutes, depending upon the desired concentration strength. After the concentration of the *Crocus sativus* is achieved, the steeping constituents are removed from the infused solvent, for example by a straining process. The extract is then cooled to about 25° C. at which it is then placed within a container or chamber for inhalation therapy.

The mixture comprising the solvent and *Crocus sativus* is preferably stirred until the desired concentration is achieved, as evidenced by the preferred color change of the steeped mixture. In a preferred embodiment, the mixture of the *Crocus sativus* and solvent is steeped such that the color of the mixture changes to an orange color having a Pantone® identification number of 144C. Typically, the steeping mixture changes from a brown color, having a Pantone® identification number ranging from 127C to 129C, to a darker brown, having a Pantone® identification number ranging from 135C to 137C or in the Pantone® identification number 1375 color family, and then finally to an orange color, having a Pantone® identification number of 144C.

The Pantone® Color Matching System is a standardized color reproduction system that may be used to accurately reproduce the intensity and hue of a color. The system uses standardized color mixtures to accurately replicate various shades and intensity of colors. The Pantone® Matching System may be used as a means by which to assess readiness of the steeped medium for use in inhalation therapy. Pantone Guides provide a number of color swatches for color matching. "Pantone" is a registered trademark of Pantone LLC, of Carlstadt, N.J.

Figure 2:
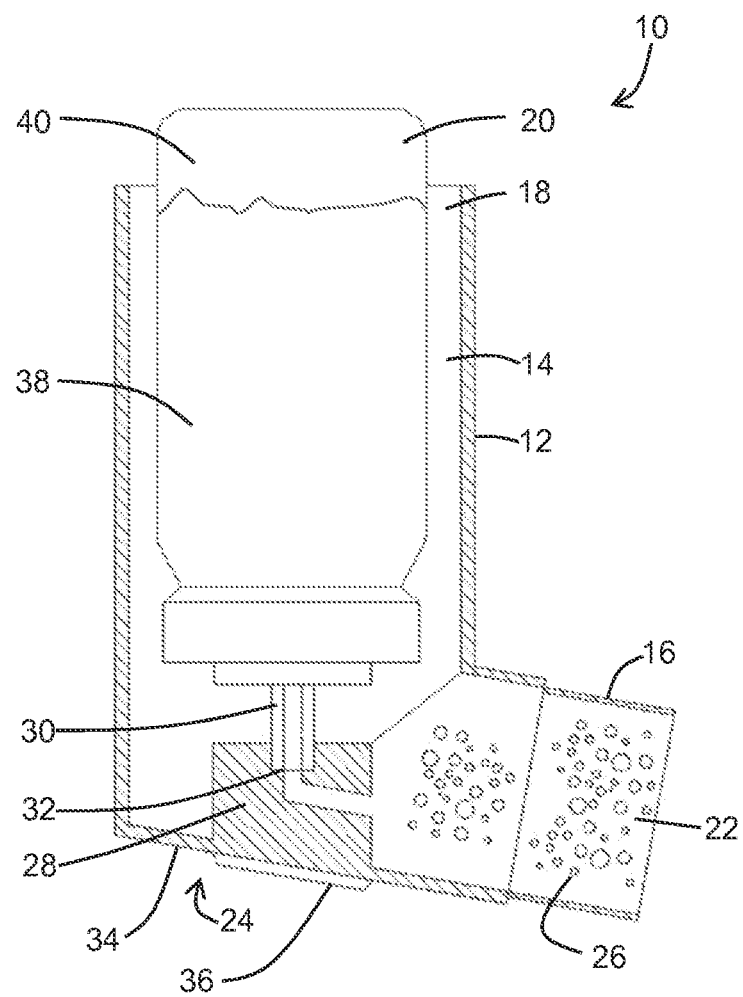

FIG. 2 illustrates an embodiment of an inhaler 10 that may be used to deliver the *Crocus sativus* infusion or medicinal extract. In a preferred embodiment, the inhaler 10 comprises a housing 12 having an opening 14 that extends to a mouth piece 16. In a preferred embodiment, a distal end 18 of the opening 14 is designed to receive an inhaler container or vessel 20, such as a sealed inhaler canister and an opening proximal end 22 that comprises the inhaler mouth piece 16. The inhaler mouth piece 16 is designed to channel the released therapeutic aerosol comprising the *Crocus sativus* mixture to a patient. In addition, the inhaler 10 comprises an actuation mechanism 24. The actuation mechanism 24 activates the release of a therapeutic aerosol 26 from within the inhaler container or canister 20.

In a preferred embodiment, the actuation mechanism 24 comprises a moveable mechanism member 28 that operates a container release valve 30 that enables the contents within the container to expel out. In a preferred embodiment illustrated in FIG. 2, the moveable mechanism member 28 compresses against a distal end 32 of the release valve 30. When compressed, the contents contained within the inhaler container 20 expel out through the valve 30. The movable mechanism member 28 may comprise a moveable portion of a sidewall 34 of the housing 12 or may comprise an actuation button 36 that when depressed, causes the release of the contents contained within the inhaler container 20.

In a preferred embodiment, a medicinal therapeutic mixture 38 comprising the *Crocus sativus* extract, infusion or combination thereof, is contained within the sealed inhaler container or canister 20. In addition to the *Crocus sativus* extract, other solvents or medicinal compounds such as ethyl alcohol, glycerin and tinctures may be mixed with the *Crocus sativus* and contained within an interior 40 of the container 20. In addition, a propellant such as a chlorofluorocarbon or a hydrofluoroalkane may be comprised within the container 20. The propellant is preferably mixed with the medicinal therapeutic mixture 38 comprising the *Crocus sativus* extract. In addition, the propellant provides an aerosol medium with which the *Crocus sativus* extract or infusion mixture thereof is expelled from within the container 20. Once expelled from the container 20, the aerosol *Crocus sativus* 26 travels through the mouth piece 16 of the inhaler 10, where it is thus inhaled by a patient.

Figure 3A:
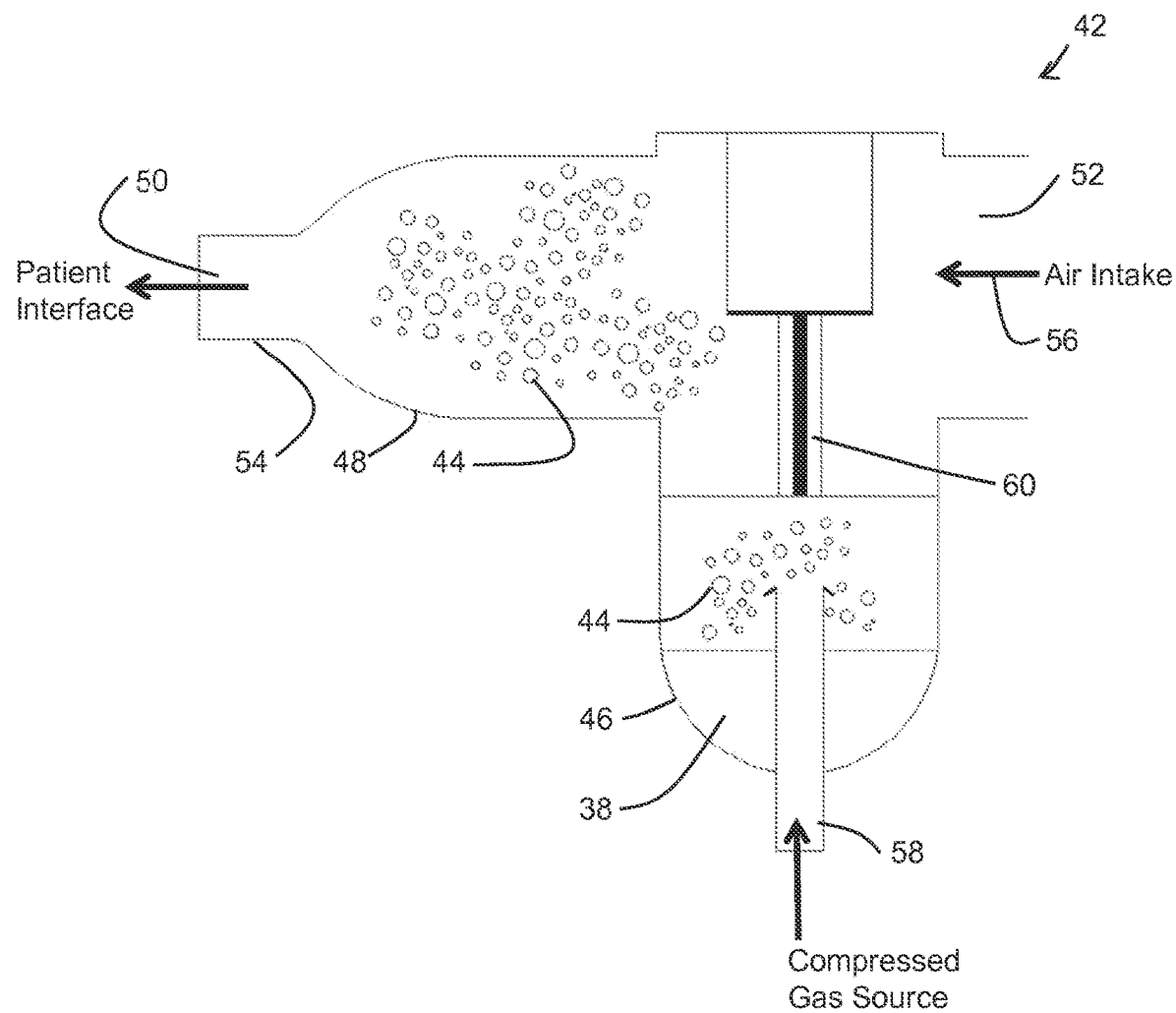

FIG. 3A illustrates a generalized embodiment of a jet nebulizer 42 that may be used to create an aerosol 44 of the medicinal therapeutic mixture 38 comprising the *Crocus sativus* extract. In a preferred embodiment, the jet nebulizer 42 comprises a reservoir 46 within which the therapeutic mixture 38 comprising the *Crocus sativus* extract or infusion may reside. In addition, the jet nebulizer 42 comprises a housing 48 having first and second openings 50, 52. In a preferred embodiment, the first opening 50 extends to a mouth piece 54 that interfaces with a patient. The second opening 52 comprises a gas intake end 56. In a preferred embodiment, ambient air enters through the gas intake end 56. As shown in the figure, a compressed gas carried by a tube 58 is introduced into the reservoir 46. The compressed gas forces the medicinal therapeutic mixture 38 comprising the *Crocus sativus* through a baffle 60 at which pressure from the air intake end 56 creates the aerosol mist 44 comprising the *Crocus sativus*. The aerosol mist 44 is then inhaled by a patient through the mouthpiece 54. In a preferred embodiment, the compressed gas may comprise ambient air, oxygen, an inert gas, or combinations thereof.

Figure 3B:
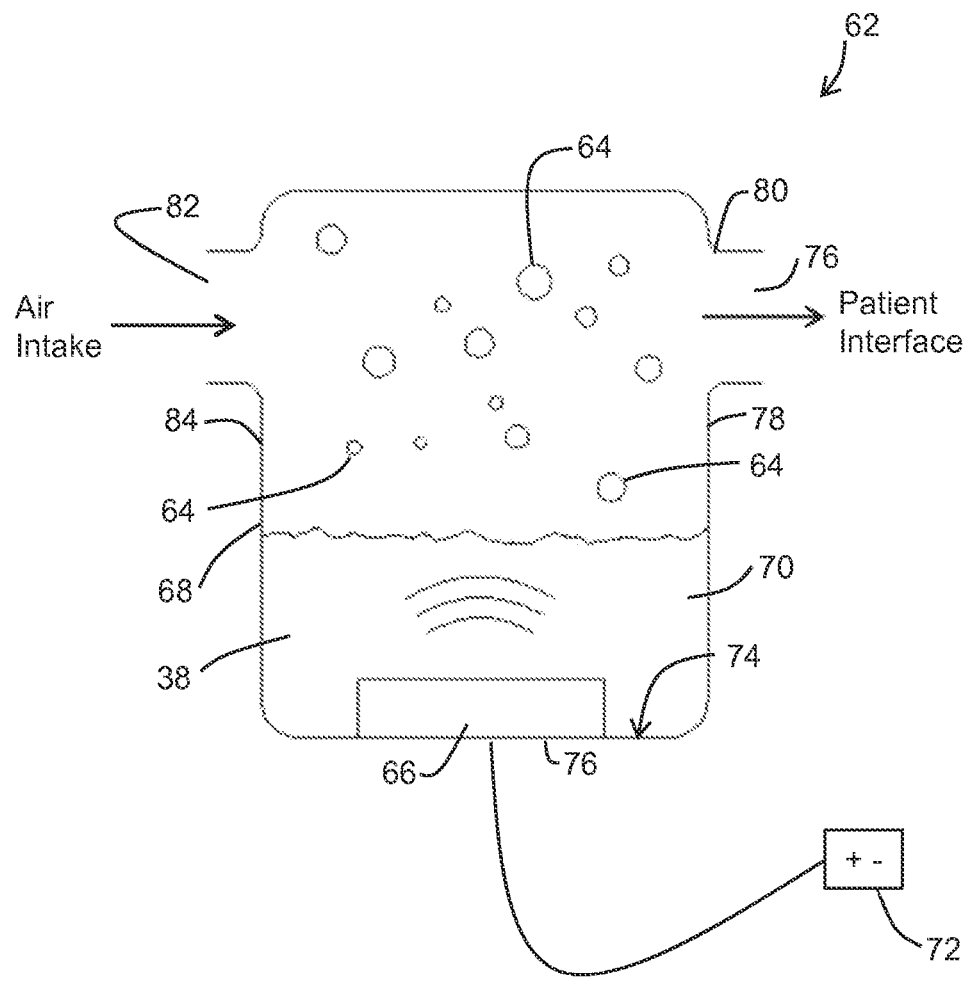

FIG. 3B illustrates a generalized embodiment of an ultrasonic nebulizer 62 which may be used to produce a therapeutic aerosol 64 of the therapeutic mixture 38 comprising the *Crocus sativus* extract or infusion thereof. As previously mentioned, the ultrasonic nebulizer 62 utilizes an oscillating or vibrating transducer 66 that creates the aerosol particles 64. In this case the aerosol particles 64 comprise the infused *Crocus sativus* mixture. As shown, the ultrasonic nebulizer 62 comprises a housing 68 having a reservoir portion 70. In a preferred embodiment, the *Crocus sativus* infusion mixture 38 resides within the reservoir portion 70. In addition, the transducer 66, such as a piezoelectric transducer, is submerged within the *Crocus sativus* infusion mixture. In a preferred embodiment, the transducer 66 is positioned on an interior surface 74 of a bottom sidewall 76 of the reservoir 70. Vibration of the transducer 66 within the therapeutic mixture 38 comprising the *Crocus sativus* infusion mixture creates a plurality of aerosol particles 64 which escape from the reservoir container 70. As shown, electrical power is supplied to the transducer 66 through an electrically connected power source 72.

In addition, as shown, the nebulizer 62 has a first opening 76 that extends through a sidewall 78 of the housing 68. The first opening 76 extends to a mouth piece 80 that interfaces with a patient. A second opening 82 opposed from the first opening 76, extends through a second portion 84 of the housing sidewall 78. The second opening 82 comprises an air intake designed to receive a gas such as compressed air, oxygen, an inert gas or combinations thereof. Pressure created by the air or gas entering the intake opening 82 forces the aerosol 64, created by the transducer 66, out through the mouthpiece 80 where it is inhaled by a patient.

Figure 4:
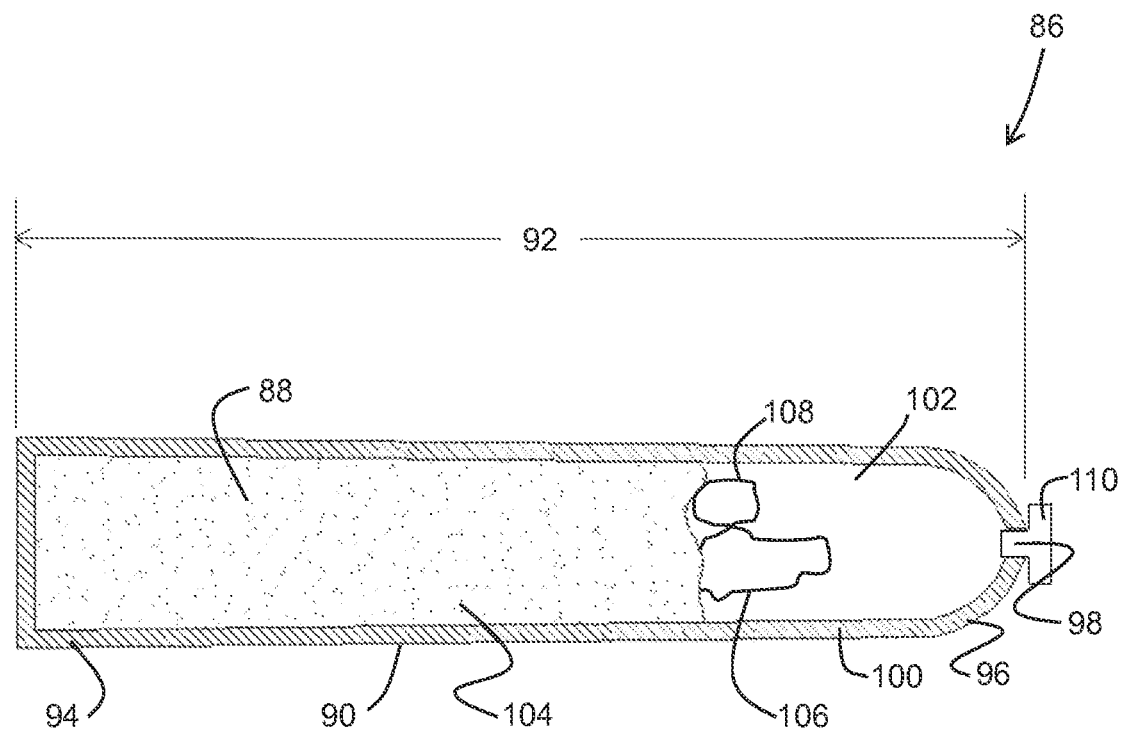

In another embodiment, a portable inhaler device 86 such as the embodiment shown in FIG. 4 may be used as a vehicle in which a therapeutic mixture 88 comprising the *Crocus sativus* is inhaled. The inhaler 86 comprises a housing 90 having an elongated length 92 that extends between opposing first and second housing ends 94, 96. In a preferred embodiment, the inhaler housing 90 comprises an enclosure formed in an elongated tubular form. In a preferred embodiment, the inhaler housing 90 extends to an annular opening 98 at the second housing end 96. The opening 98 extends through a housing sidewall 100 and provides access to an interior housing region 102. In addition, the opening 98 acts as the interface to the patient. In a preferred embodiment, the inhaler 86 shown in FIG. 4, is positionable within a nose of a patient, wherein the medical therapeutic mixture 88 therewithin is inhaled. Alternatively, the opening 98 of the inhaler 86 may be positioned within the patient's mouth to facilitate inhalation of the *Crocus sativus* extract.

In a preferred embodiment, the therapeutic mixture 88 comprising the *Crocus sativus* extract, infusion mixture or compound thereof resides within the interior region 102 of the inhaler 86. In addition, a mixture comprising ethyl alcohol, a wax, petroleum jelly, polymeric material or combinations thereof may be mixed with the *Crocus sativus* to thus form a therapeutic compound 104 that is positionable within the interior 102 of the inhaler housing 90. A wick 106 or a fillable packaging 108 may reside within the inhaler housing 90. Preferably at least a portion of the wick 106 may reside within the *Crocus sativus* comprising mixture 88 or compound 104. The wick 106 may be made of cotton or other absorbent material. The wick 106 may also be soaked in the saffron infusion or extract or may be added by droplets to the wick 106 (from 5 to 30 or more) and then assembled for inhaling.

A cap 110 may be positioned over the opening 98 to prevent evaporation or contamination of the therapeutic mixture 88 or compound 104 residing within the housing 90.

The inhaler housing 90 may be made of a polymer, plastic, metal, cardboard, glass, composite or other such structural material.

In another embodiment, the inhaler 86 may house commercially available saffron that may be packaged within the fillable packing or secondary container 108 such as, but not limited to, a cotton pillow, a woven or non-woven fabric, or an absorbent paper pouch, that resides within the nose inhaler housing 90. In a preferred embodiment, the saffron within the secondary container 108 may be activated with water (or other solvent such as ethyl alcohol). Individuals may conduct repeated periodic inhalation until therapeutic relief is achieved.

In a preferred embodiment, the secondary container 108 may comprise a pouch, bag or a pillow that encloses an amount of *Crocus sativus*. The secondary container 108 may be constructed by enclosing an amount of an extract constituent, such as *Crocus sativus* within about a 3 cm to 4 cm by a 1 cm to 2 cm area of material on three sides. The secondary container 108 is formed by, for example but not limited to, folding or sealing three of the sides of the material together. In a preferred embodiment, about 0.5 g to about 3 g of *Crocus sativus* stigma or other saffron form is inserted into this 3 sided sealed package. After the saffron is positioned inside the container 108, the fourth side of the material is sealed along with the other three sides. The secondary container 108, comprising the extract constituent is then placed within the housing 90 of the inhaler 86. About 3 ml to 9 ml of distilled water, preferably having a temperature greater than 10° C. is then poured onto the filled secondary package 108.

In addition to vaporizing the *Crocus sativus* infusion or extract into an aerosol mist, as previously described, a concentrated form of a medicinal compound 104 may be made by combining the *Crocus sativus* with a variety of non-limiting oils, waxes, gels, petroleum jelly, ethyl alcohol, or other solvents. In this embodiment, the *Crocus sativus* may be mixed with a combination of these oils, waxes, and/or alcohols to create a concentrated hardened medicinal compound of *Crocus sativus*. In an embodiment, the medicinal compound 104 may be positioned within the inhaler 86 illustrated in FIG. 4. In addition to vaporizing the hardened medicinal *Crocus sativus* compound, it is further contemplated that the medicinal compound 104 may be ingested. Such an ingestible *Crocus sativus* comprising compound may contain ingestible materials such as, but not limited to ingestible oils, waxes, ethyl alcohol, flavorings, herbs such as cinnamon, turmeric, mint as well as vitamins, water and alcohol soluble additives and/or hardeners. Furthermore, it is contemplated that the *Crocus sativus* extract or infusion mixture may be ingested itself or applied to the skin. Such a mixture for topical applications may also comprise a cream or oil designed for application to the skin.

In an embodiment, vaporization of the medicinal therapeutic mixture 38 comprising the *Crocus sativus* infusion, and/or the *Crocus sativus* comprising medicinal compound 104, may be accomplished through contact with a heat source (not shown) such as a heated surface. A heated or non-heated forced air source (not shown) may also be used in combination with the heat source to facilitate vaporization of the *Crocus sativus* comprising mixture. The emanation of such a vapor resulting from the heating of the medicinal compound 104 or mixture 38 may be directly inhaled from a vaporization device such as a humidifier (not shown), through a connector device (not shown), such as but not limited to a mask, a tube, a balloon or a nose piece that is connectable to the vaporization device (not shown). The Crocus sativus medicinal compound or infusion is preferably deposited within a chamber of the vaporization device such that it is in contact with the heat source.

Vaporizers typically reach temperatures between about 680° C. (360° F.) and 806° C. (430° F.) which is a temperature capable of vaporizing the Crocus sativus infusion mixture 38 or medicinal compound 104. Digitally controlled vaporizers may be used by individuals preferring to set specific vaporization temperatures. Generally, temperatures less than 842° C. (450° F.) are used as organic matter burns above that temperature, potentially contaminating the vapors with toxic materials.

In another embodiment, a humidifier (not shown) containing the infused saffron 38 or medicinal compound 104 may be placed in a room without the aid of a connector device (not shown). In this embodiment, the vaporized Crocus sativus comprising infusion mixture 38 or medicinal compound 104 is emanated through the air surrounding the humidifier. Inhalation of the saffron infused steam may be achieved by the individual's presence within the room being humidified. Inhalation can occur while sleeping, working, or other activity being conducted within a room to provide treatment of a medical ailment, such as reducing premenstrual symptoms.

In another embodiment, the Crocus sativus extract 38 and/or medical compound 104 may be vaporized using an electric cigarette 112 as shown in FIG. 5. The electronic cigarette 112 typically comprises a heating element 114, i.e., an atomizer that heats a liquid or material contained within an electronic cigarette container or cartridge 116 until it reaches its vaporization point. The mixture 38, in this case, the Crocus sativus comprising extract or infusion mixture or compound 104, as previously discussed, is contained within the electronic cigarette container or cartridge 116 that resides within an electronic cigarette housing 118. A micro-controller 120 connected to an electrical power source 122 may be used to activate the atomizer 114 and vaporize the Crocus sativus extract contained therewithin. An operating indicator 130 such as a light emitting diode (LED) or other light source may be controller by the micro-controller 120 to indicate that the heating element 114 is operating.

In a preferred embodiment, heat emanating from the heating element 114 heats the electronic cigarette container 116, converting the therapeutic mixture 38 comprising the Crocus sativus extract or infusion mixture into an aerosol particle vapor 124 that is inhaled by a user. Alternatively, the heating element 114 may also heat the Crocus sativus comprising compound 104 which may be contained therewithin, thus converting it into aerosol particle vapor 124. The aerosol vapor particles 124 are delivered through an opening 126 of the housing 118 which serves as a mouth piece 128 through which a user may inhale, thus forcing the vapor 124 into the lungs of the user. The electronic cigarette delivery concept provides a vapor, or steam comprising Crocus sativus that may be inhaled into the lungs to provide instantaneous therapy and relief of the various medical ailments previously discussed. The above detailed description and examples are intended for purposes of illustrating the invention and are not to be construed as limited.

What is claimed is:

1. A primary container suitable for delivering a medicinal formulation for inhalation therapy, the primary container comprising:
   a secondary enclosure positioned within the primary container, wherein the enclosure comprises an absorbent material;
   a mixture comprising Crocus sativus extract residing within the secondary enclosure, wherein the adsorbent material encases the mixture within the secondary enclosure; and
   wherein the primary container is receivable within an electronic cigarette.

2. The primary container of claim 1 wherein a release valve is positioned within an opening of the primary container, wherein the release valve is capable of opening and closing the primary container opening.

3. The primary container of claim 1 wherein the primary container is a canister capable of withstanding a vapor pressure contained within an interior therewithin.

4. The primary container of claim 1 wherein the mixture comprises a solvent selected from the group consisting of water, ethyl alcohol and combinations thereof.

5. The primary container of claim 1 wherein the primary container is receivable within an inhaler device.

6. The primary container of claim 1 wherein a propellant resides within the secondary enclosure.

7. The primary container of claim 4 wherein the mixture comprises a concentration of at least 0.01 mg of Crocus sativus extract to about 1 ml of solvent.

8. The primary container of claim 1 wherein the mixture further comprises an herb, a petroleum jelly, a spice, a vitamin, turmeric, lavender, cinnamon, mint, and combinations thereof.

9. The primary container of claim 1 wherein the secondary enclosure comprises a bag, a pillow, or a pouch.

10. A primary container suitable for delivering a medicinal formulation for inhalation therapy, the primary container comprising:
    a secondary container positioned within the primary container, wherein the secondary container comprises an adsorbent material;
    a mixture comprising Crocus sativus extract residing within the secondary container, wherein the adsorbent material encases the mixture within the secondary container; and
    wherein the primary container is receivable within an electronic cigarette.

11. The primary container of claim 10 wherein the medicinal formulation further comprises an aromatic, an herb, a hydrocarbon, a flavoring, a glycerol, a spice, a petroleum jelly, an oil, a tincture, a vitamin, or a combination thereof.

12. The primary container of claim 10 wherein the medicinal formulation comprises a solvent selected from the group consisting of water, ethyl alcohol, vinegar, and combinations thereof.

13. The primary container of claim 10 wherein the primary container is receivable within an inhaler device or an electronic cigarette.

14. The primary container of claim 10 wherein the secondary container comprises a bag, a pillow, or a pouch.

15. A primary container suitable for delivering a medicinal formulation for inhalation therapy, the primary container comprising:
    a secondary container positioned within the primary container, wherein the secondary container comprises an adsorbent material selected from the group consisting of cotton, a paper, a woven fabric, a non-woven fabric, and combinations thereof;
    a mixture comprising Crocus sativus extract residing within the secondary container, wherein the adsorbent material encases the mixture therewithin; and
    wherein the primary container is receivable within an electronic cigarette.

16. The primary container of claim 15 wherein the medicinal formulation further comprises an aromatic, an herb, a hydrocarbon, a flavoring, a glycerol, a spice, a petroleum jelly, an oil, a tincture, a vitamin, or a combination thereof.

17. The primary container of claim 15 wherein the medicinal formulation comprises a solvent selected from the group consisting of water, ethyl alcohol, vinegar, and combinations thereof.

18. The primary container of claim 15 wherein the primary container is receivable within an inhaler device or an electronic cigarette.

19. The primary container of claim 15 wherein the secondary container comprises a bag, a pillow, or a pouch.

* * * * *